US006445957B1

(12) United States Patent
Bolmsjo

(10) Patent No.: US 6,445,957 B1
(45) Date of Patent: Sep. 3, 2002

(54) METHOD AND DEVICE FOR SUPPLY FOR HEAT

(75) Inventor: Magnus Bolmsjo, Lund (SE)

(73) Assignee: Prostalund Operations AB (SE)

( * ) Notice: Subject to any disclaimer, the term of this patent is extended or adjusted under 35 U.S.C. 154(b) by 0 days.

(21) Appl. No.: 09/509,735

(22) PCT Filed: Sep. 29, 1998

(86) PCT No.: PCT/SE99/01729

§ 371 (c)(1),
(2), (4) Date: Sep. 8, 2000

(87) PCT Pub. No.: WO99/17689

PCT Pub. Date: Apr. 15, 1999

(30) Foreign Application Priority Data

Oct. 2, 1997 (SE) .............................................. 9703608

(51) Int. Cl.⁷ ............................. A61F 2/00; A61B 18/04
(52) U.S. Cl. ......................... 607/101; 607/102; 606/29
(58) Field of Search .............................. 606/27–29, 41, 606/42; 607/96–99, 101, 102, 104, 105, 113, 116

(56) References Cited

U.S. PATENT DOCUMENTS

| 4,825,880 | A | * | 5/1989 | Stauffer et al. ............. 607/156 |
| 5,084,044 | A | * | 1/1992 | Quint ........................... 606/27 |
| 5,558,672 | A | | 9/1996 | Edwards et al. | |
| 5,599,294 | A | * | 2/1997 | Edwards et al. ............... 604/22 |
| 5,628,771 | A | * | 5/1997 | Mizukawa et al. .......... 607/102 |
| 5,902,251 | A | * | 5/1999 | vanHooydonk ............. 600/549 |

FOREIGN PATENT DOCUMENTS

| EP | 0 694 291 | 9/1998 |
| WO | WO 95/09577 | 10/1993 |
| WO | WO 95/19142 | 1/1994 |
| WO | WO 96/36288 | 5/1996 |

OTHER PUBLICATIONS

WO 96/36288, PCT Application, Nov. 21, 1996.*

* cited by examiner

Primary Examiner—Roy D. Gibson
(74) Attorney, Agent, or Firm—Mathews, Collins, Shepherd & McKay, P.A.

(57) ABSTRACT

A device for supply of heat to body tissue, comprising a heating device (10) and a first temperature transducer (11) which is insertable in the body tissue, the heating device (10) being connected with an energy supply unit (13) governed by a control unit (14) via a catheter for treatment (12) which is insertable in a body cavity and said first temperature transducer (11) being operatively connected to the control unit (14). The control unit (14) is operatively connected with first memory means (15) for storage of data corresponding to the survival of cells as a function of cell temperature. An input device (16) is operatively connected to control unit (14) to enter data such as desired volume/weight of body tissue to which heat is to be supplied to such an extent that the cells of the tissue die, and the control unit (14) being operatively connected to calculation instrument (17) for determining volume and weight of such body tissue whose cells have died as a function of temperature in the tissue at a certain distance from heating device (10).

15 Claims, 1 Drawing Sheet

METHOD AND DEVICE FOR SUPPLY FOR HEAT

THE SCOPE OF THE INVENTION

The invention concerns a device for supply of heat to body tissues according to the preamble of Patent claim 1.

With certain kinds of conditions caused by diseases involving unnatural growths in tissues, treatment with heat gives a good result after treatment. The tissue is heated to the degree that it dies. Examples of disease conditions of this kind are certain types of cancer and benign prostate hyperplasia, BPH. With treatment certain parts of the tissue are heated so that death of the tissue occurs, while other parts of the tissue must or should be protected. The conditions of disease which are primarily focused on here are those which occur in tissue surrounding cavities in the body. As examples beyond that mentioned above cancer of the esophagus, trachea, urethra, and intestine can also be mentioned.

Corresponding conditions of disease can also occur in animals, where similar treatment can be applied. Above all, treatment of domestic animals such as, for example, dogs can become topical.

STATE OF THE TECHNOLOGY

In order to produce heat, different devices can be employed. Laser, microwave, and radio frequency antennas are usually used. A method using the insertion of a container with liquid into the bodily cavity is also known. The liquid expands the container so that good contact against the surrounding tissue is achieved. The liquid is then heated either by supplying warm liquid through a circulating system or by supplying energy to a heating device within the container from which heat is transferred in some way to the liquid and then to the tissue.

Since the volume of the tissue which will be treated varies as well as the ability to absorb heat in this tissue and adjacent tissue, which will not be treated, it is appropriate that continuous monitoring occur during treatment. When treatment is in progress, the heating of tissue occurs. The heating should occur within certain temperature ranges for the best result of the treatment. At too high a temperature unnecessarily great damage occurs in the tissue and at too low a temperature the desired result of treatment does not occur.

It is common that the device for heating incorporates some form of temperature sensor that is arrayed on the element inducing heating in order to monitor the temperature in adjacent tissue. A disadvantage of this design is that the temperature sensor gives information more on the temperature of the element than on the temperature of the tissue.

An example of this type of heating device is shown and described in EP 0 370 890. The device encompasses a catheter contained in a microwave antenna that is embodied to emit radio energy to the tissue surrounding the antenna. The catheter is also provided with a cooling channel for cooling the tissue that is located closest to the catheter. In the catheter a temperature transducer is located for reading the temperature of the catheter. The detected temperature is thus not in agreement with the temperature of the tissue that is being treated.

A more developed method of temperature detection is shown and described in PCT/SE96/00649. In order to be able to register the rise of temperature directly in the tissue to be treated, a first temperature detection instrument according to PCT/SE96/00649 is connected with a first carrier. The carrier is led through a channel in the catheter and is devised to be extendable through an opening in the catheter. In the opening of the catheter a control device for the carrier is appropriately arrayed so that the carrier is directed into the tissue at the desired angle in relation to the catheter. The treatment carried out with the above-mentioned microwave device is often called TUMT (TransUrethral Microwave Thermotherapy).

Either the carrier or the temperature detection instrument is equipped with a tip that facilitates penetration into the tissue. The temperature detection instrument can be conventionally embodied as a resistive transducer or a semiconductor. The cabling required for transducers of this type is done via channels in the catheter. If a transducer of the optical type is used, a fiber-optic guide is provided through a channel in the catheter.

According to the devices described above and according to other known techniques, the attending physician normally determines the duration and temperature of treatment. In spite of the possibility to conduct continuous temperature detection, there are problems in securing satisfactory results of treatment during the process of treatment, since the process of healing can take up to several weeks or months. It is also difficult to adjust a treatment in process to new conditions, for example, pain arising in the patient, and to judge how the treatment in general should be adjusted to current physical conditions in the patient.

THE INVENTION IN SUMMARY

An object of the invention is to produce a device for supply of heat to body tissue, whereby the disadvantages mentioned above are essentially eliminated. This object is achieved according to the invention by the features indicated in the Patent claims 1 through 10.

According to the invention there is also the possibility of adjusting the supply of heat beforehand in different ways and to predict the result better. A device according to the invention is used in order to calculate the temperature distribution in the whole prostate based on information on it at certain points measured intra-prostatically and information on the distribution of the energy absorption in body tissue from an energy or heat source. The temperature distribution is determined on the basis of the relation between the temperature in the tissue and absorbed energy, blood flow, and heat conduction. Through continuous measurement of the temperature and the time during which heat is applied, and with continuous monitoring of the temperature distribution in relation to information on the survival of cells undergoing thermal exposure, the amount of tissue destroyed at certain points in time during the exposure is determined.

In a preferred embodiment the temperature distribution and destruction of tissue is continuously presented as image and text on a display, so that the attending physician can constantly be informed on current conditions. Heat is supplied to the tissue until a portion of the tissue that can be adjusted for has been destroyed.

Further advantages and special features of the invention can be seen by the following description, drawings, and dependent patent claims.

BRIEF DESCRIPTION OF THE DRAWINGS

The invention will now be described in more detail with the aid of examples of embodiments with reference to the attached drawings on which

DESCRIPTION

Figure 1:
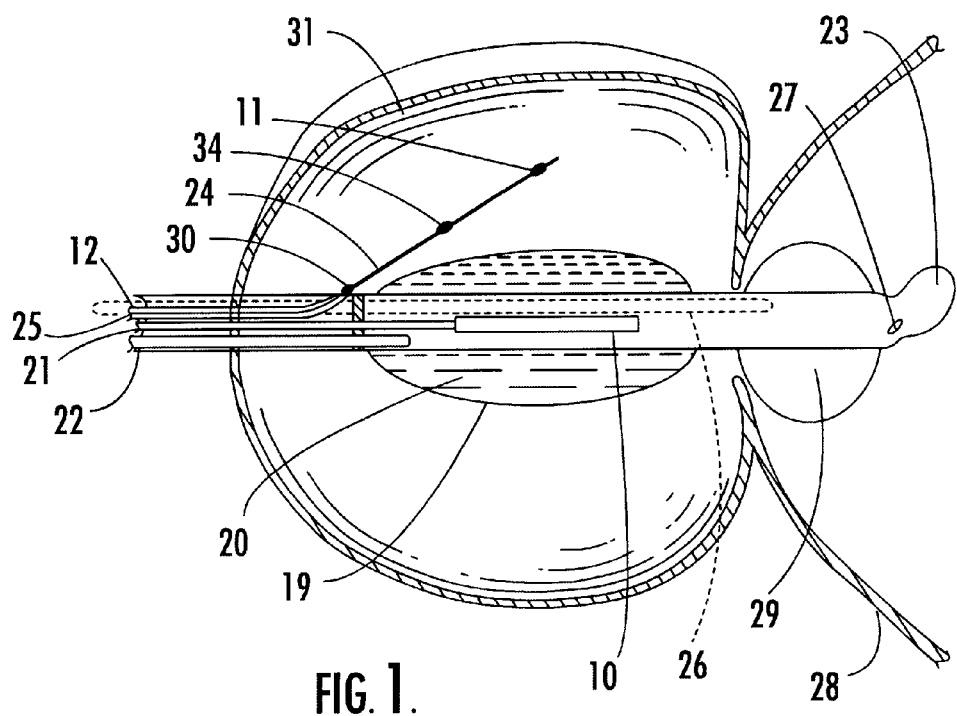
FIG. 1 is a longitudinal sectional view of a catheter for treatment that can be included in a device according to an embodiment of the invention

A catheter for treatment 12 is inserted into the urethra according to FIG. 1, so that a tip 23 has penetrated urine bladder 28. A bladder or balloon 29 connected to the catheter for treatment is expanded inside urine bladder 28 and prevents inadvertent withdrawal of the catheter for treatment during the duration of the procedure. The active part of the catheter for treatment is thus located centrally in the tissue that is to be treated, in this case prostate 31. The catheter for treatment 12 is ductile and flexible in order to be introduced through the urethra to the site of the treatment.

In FIG. 1 a container 19 is shown expanded to its working volume by liquid 20 which has been fed into it under pressure. Container 19 can be pear-shaped in the longitudinal direction of the catheter for treatment with a thicker section in the part which is turned toward the urine bladder or more symmetrically in the axial direction according to the embodiment shown in FIG. 1. The shape follows or is fitted to the form of the urethra in this section. Container 19 is located on the outside of the catheter for treatment and appropriately has its larger portion of container 19 on the lower side of the catheter for treatment. With expansion of container 19 the catheter for treatment is lifted upwards, which in the body means that the distance between a heating device 10 located in container 19 and the rectum increases. Liquid 20 is directed through channel 22 devised as a tube which extends through catheter for treatment 12.

In order to be able to follow the temperature development in the tissue during heat treatment a first temperature transducer 11 is located on a carrier 24. Carrier 24 is designed to be advanced through a channel or conduit 25, which runs through the catheter for treatment. Carrier 24 or temperature transducer 11 is preferably provided with, or as, a tip which can penetrate in part a membrane or wall in the catheter for treatment and in part the tissue. Conduit 25 is embodied so that carrier 24 with temperature transducer 11 is advanced out of the catheter for treatment at a suitable angle and can be extended to a suitable radial distance from the catheter for treatment. It is also possible to provide a specially angled instrument in the terminal section of conduit 25 in order to achieve the desired angling of temperature transducer 11. Catheter for treatment 12 can also be equipped with another temperature transducer 30. Information on the temperature near container 19 or in tissue absolutely closest to catheter for treatment 12 is obtained from the second temperature transducer 30. In the embodiment according to FIG. 1 and FIG. 2 the device according to the invention is also equipped with a third temperature transducer 34. Third temperature transducer 34 is preferably also located on carrier 24 between first temperature transducer 10 and second temperature transducer 30, so that the temperatures can continuously be determined at a specified distance from catheter for treatment 12.

Liquid channel 26 is also incorporated in the catheter for treatment. It pens into balloon 29 and through it liquid can be directed for expansion of balloon 29 when the catheter for treatment is in place. Liquid channel 26 is also used to empty balloon 29 at the conclusion of treatment and before the catheter for treatment is withdrawn from the urethra. A conventional syringe or similar is preferably used for insertion of liquid and for emptying balloon 29.

A feed cable 21, by means of which heating device 10 is supplied with energy, is warmed as a result of heat loss. In order to avoid injury of tissue beyond the area of treatment, for example, on the sphincter that surrounds the urethra outside the prostate, feed cable 21 is cooled. This is done by providing cooling channels in catheter for treatment 12, preferably around feed cable 21. In an embodiment according to the invention the cooling channels have a limiting wall at which the cooling liquid circulating in the cooling channels returns. In this manner cooling of heating device 10 itself is avoided, which in turn means that the power, which needs to be supplied from an energy supply unit 13, can be less. With lower levels of power the risk of malpractice and injury to healthy tissue is lessened.

Heating of tissue thus occurs in part at a closer distance through heating of the liquid contained in the container, which radiates heat directly to adjacent tissue, and in part at longer distance through electromagnetic radiation. The total area of treatment is greater than with conventional heating, which means that larger sections of tissue can be reached.

At high temperatures in the range of 90–150° C. the tissue also hardens and forms a crust. The crust can prevent or lessen problems that can occur if the prostate gland swells in connection with the treatment. Since the highest temperature is reached in tissue closest to container 19, the part of the urethra that passes through the prostate at the area of treatment will be affected to a high degree and injured. This part of the urethra, however, restores itself relatively quickly.

In a preferred embodiment heating device 10 comprises a microwave antenna. Since the urethra is completely filled-in the area of treatment and no free space remains, the fit of the microwave antenna against the tissue will also be very good. The liquid in container 19 is selected so that it has essentially or completely the same characteristics as the prostate tissue as regards propagation of microwaves. The adjustment of impedance between the antenna and the tissue is thus also very good, which simplifies dimensioning of the antenna and energy supply unit and facilitates the setting of microwave power.

When treatment is finished, the energy supply to heating device 10 is interrupted and the container is emptied and allowed to return to normal body temperature. It is not suitable to remove the catheter for treatment as long as the container has a temperature such that injuries could occur with the passage of the container through the body. The temperature of container 19 is for this reason monitored continually so that removal of the catheter for treatment can occur as soon as the desired temperature has been reached.

In cases of treatment involving the prostate or urine bladder, whereby catheter 12 having a tip is introduced into urine bladder 28, drainage of urine and possibly of other liquid from the urine bladder can occur through a drainage channel provided in catheter 12. The drainage channel runs through all of catheter 12 and ends with opening 27 near the tip of catheter 12. With certain types of treatment, it can be suitable to leave catheter 12 in place for a certain time after treatment. It is the function of the drainage channel to drain the urine bladder even during this time.

The treated and dead tissue is reabsorbed or rejected and eliminated with urine. A cavity in the prostate caused by the removal of tissue ensures the correct passage of urine. The cavity at first has a form that corresponds to the form of container 19 at the time of treatment.

As a complement to, or part of, the heat treatment according to the above, some forms of medicine can be introduced into liquid container 19. Liquid container 19 is modified in such cases so that it permits the throughput of the medicine. Liquid container 19 is preferably embodied so that the medicine can diffuse through the wall of liquid container 19, but it is also possible to provide seepage channels or similar in the wall. According to one treatment painkillers can be included in the liquid. Even other medicines effecting direct treatment can be used.

According to an alternative embodiment, liquid container 19 is not included. In such an embodiment heating occurs directly by means of heating device 10, which in this case is provided to radiate energy which can be absorbed by the tissue. Microwave radiation is preferably employed with a heating device 10 that includes an antenna. Lasers and other types of radiation sources can also come into question.

Figure 2:
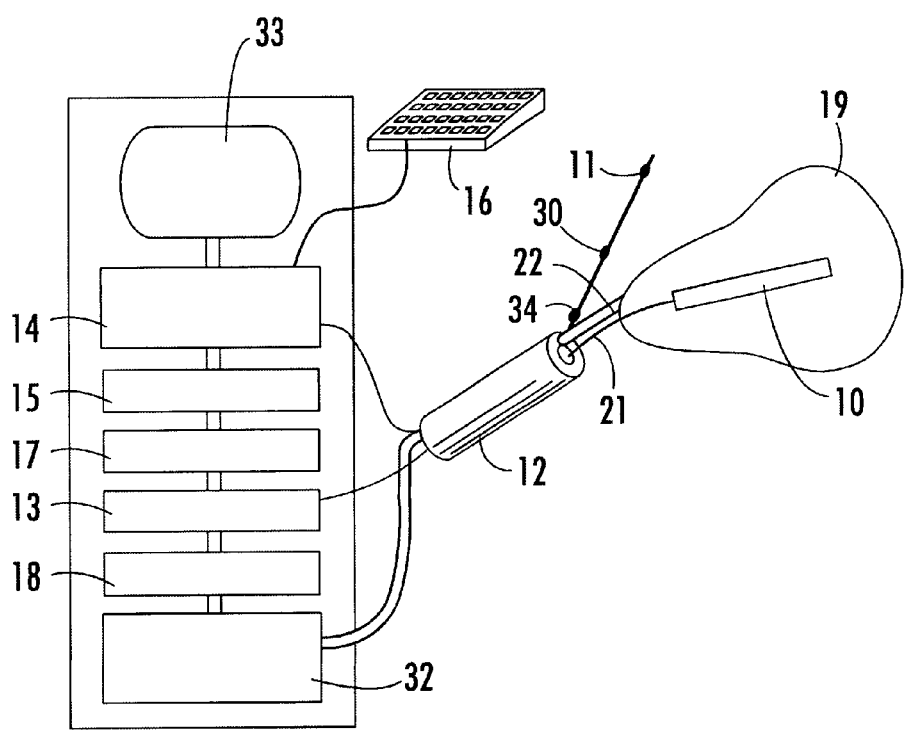
FIG. 2 is a principal block diagram, which shows a device according to an embodiment of the invention.

The block diagram in FIG. 2 shows schematically the different functional blocks which can be included in a treatment assembly with a catheter for treatment according to the invention. As was indicated above, heating device 10 is supplied with energy from an energy supply unit 13. A central control unit 14 is operatively connected with energy supply unit 13 and a display unit 33 together with an apparatus for liquid supply 32. Control unit 14 is additionally operatively connected with an input device, for example, in the form of a keyboard 16. Control unit 14, keyboard 16, and display unit 33 can also be included in a conventional computer with monitor and keyboard.

For treatment with TUMT and similar methods of treatment the temperature of the tissue is determined to the greatest degree by three different processes: i) generation of heat by absorption of microwave energy or another source of radiated energy, ii) heat distribution as a result of heat conduction in the tissue, and iii) heat loss as a result of the flow of blood. Parameter i) is determined by the current catheter for treatment being used, ii) can be calculated, while iii) is dependent on the patient and is unknown. The relationship is given by a known equation for bio-heat:

$$\rho c \frac{dT}{dt} = \lambda \Delta T - \varpi_b \rho_b c_b \rho (T - T_a) + Q_s + Q_m, \quad \text{(Equation 1)}$$

where $\rho$ (kg m$^{-3}$) is the density of the prostate, c (J kg$^{-1}$K$^{-1}$) is the specific heat capacity of the prostate, T (°C) is the temperature of the prostate at the time t (seconds), $\lambda$ (W m$^{-1}$ K$^{-1}$) is the heat conduction in the prostate, $\Lambda$ is the Laplace operator, $\omega_b$ is the perfusion of the tissue (m$^3$ kg$^{-s-1}$), $\rho_b$ (kg m$^{-3}$) is the density of the blood, $c_b$ (J kg$^{-1}$ K$^{-1}$) is the specific heat capacity of the blood, $T_a$ is the arterial temperature (°C), $Q_s$ (W m$^{-3}$) is generation of heat as a result of microwave absorption, and $Q_m$ (W m$^{-3}$) is the generation of heat by metabolism. The term $Q_m$ can be ignored with heat treatment. The thermal characteristics of the prostate tissue have been calculated from its water content, which is assumed to be 80%. The equation or corresponding data can be stored in memory 15, so that it can be solved continuously during the application of heat.

Since it can be assumed that microwave absorption is symmetrical in the radial orientation, cylindrical geometry was used for the numerical solution of equation 1. The finite differential technique was used for the solution. The term $Q_s$ in equation 1 was determined by the specific absorption rate (SAR, W/kg) in a certain catheter for treatment 12. A practical way to determine the specific rate of absorption is to place a TUMT catheter in a tissue-like body, for example made of the material TX-150, and measure the temperature distribution in the body after heating with a microwave output of 50W for 60 seconds. One way to measure SAR is described in detail in the *British Journal of Urology* 78 (1996), pages 564–572.

In a first memory 15 known data as to the survival of cells at different cell temperatures during different durations of treatment are stored, for example in the form of suitable equations, data tables, or similar. First memory 15 is suitably embodied so that stored data is complemented and, if necessary, corrected as new results of treatments are collected. Tissue damage caused by the treatment can be described mathematically by an Arrhenius equation according to the following:

$$\Omega = A \int e^{-E_a/(RT)} dt, \quad \text{(Equation 2)}$$

where $\Omega$ is the degree of accumulated damage during the time of treatment t, A is the Arrhenius constant ($3.1 \cdot 10^{98}$ s$^{-1}$), $E_a$ is the energy of activation of the cells, ($6.3 \cdot 10^5$ J mol$^{-1}$), R (J mol$^{-1}$K$^{-1}$) is the universal gas constant, and T (K) is the temperature of the tissue. The tissue is assumed to be destroyed at $\Omega \geq 1$.

A suitable measure is that the data are followed up at certain intervals after treatment, for example, every month for a certain period. In first memory 15, there are stored data on blood flow and other factors that affect heat absorption and heat dispersion in the type of tissue undergoing treatment. with exact data it is possible to store information in memory 15 which enables creation of a model of the tissue with respect to the factors cited above that are very close to the actual tissue. Preferably, these later data are continually complemented and corrected even after the treatment.

Before heat treatment certain current physical factors are determined, for example, the size of the prostate, the degree of narrowing in the prostate, and the distance between the prostate and the rectum. With information on these conditions a suitable type of catheter for treatment and suitable temperature for treatment are determined. In the place of duration of treatment, which according to previous devices was a decisive factor, a value is determined for the desired volume/weight of the tissue that is to be treated, so that it is destroyed. The value is given so that it is available to control unit 14, for example, by feeding it into input device 16. A highest value for temperature, or mean value for the temperature of the treatment, or a temperature range are preferably also given. The device can also be provided with further memories for storage of suitable combinations of volume/weight and temperature of the treatment. In the latter case, a norm value is automatically selected for the temperature of the treatment.

With these inputs, control unit 14 can start the treatment by supplying liquid to container 19, if that type of catheter for treatment is used, and then send a control signal to energy supply unit 13, so that heating device 10 begins to emit energy for heating of the tissue. Liquid supply apparatus 32 is used when liquid container 19 is to be filled and expanded. Control unit 14 can govern the filling so that an appropriate increase of pressure and associated compression of the prostate tissue is achieved. First temperature transducer 11 and preferably also second temperature transducer 30 and third temperature transducer 34 provide continuous information regarding the current temperature of the treatment, both near heating device 10 and at a certain distance from it in the tissue under treatment.

Control unit 14 is operatively connected with temperature transducer 11 and preferably also with transducers 30 and 34 and can, depending on the current temperature in the area of treatment, govern energy supply unit 14, so that suitable output is directed to heating device 10. By this means, it is possible to raise the temperature strongly in liquid container 19 with a good margin of safety and thus in the surrounding tissue, so that death of the tissue occurs in the desired way. Data on temperature from temperature transducers 11 and 30 can also be shown continuously in display unit 33. With the aid of input device 16 it is also possible to indicate a suitable level of output power from heating device 10, or as it can be rated from energy supply unit 13. The output level affects the temperature that the tissue receives and can in certain cases affect the level of pain experienced by the patient.

A calculating instrument 17 continuously compares data from temperature transducers 11, 30, and 34 with the data stored in first memory 15, and control unit 14 can by this means continuously calculate how the temperature varies in the prostate tissue at various distances from catheter for treatment 12. It is also possible in this way for calculating instrument 17 continuously to calculate the volume/weight of the tissue that has been treated in the desired manner and where the desired result of treatment has been achieved in the tissue.

Information calculated in this way is continuously sent to display 33, so that besides numerical data regarding the treated volume/weight, the attending physician has an image of how the treatment is proceeding. A suitable method is that a schematic image similar to that in FIG. 1 is shown on the display. Data regarding the prostate that will be treated are suitably collected beforehand, for example, by means of x-rays, ultrasound, or MR, so that the image which is shown on display unit 33 is in agreement with actual conditions. An image corresponding to the catheter for treatment that will be used is preferably superimposed over an image of the tissue.

The temperature in different parts of the prostate tissue is continuously calculated on the basis of the measured temperatures, and the current temperature is shown in the image of the prostate, for example, by means of markings in different colors. At the same time different graphs and/or tables regarding temperatures, blood flows, and volume/weight of the tissue under treatment are shown. The attending physician can in this way follow the treatment and continuously receive indications on how much tissue has been treated and where in the prostate tissue death has occurred.

A timer 18, operatively connected with control unit 14, continuously sends information on the time, so that the measured data are related to the treatment time. When one of the values for the volume/weight of the tissue being treated, as calculated by calculation instrument 17, is in agreement with the value set, the treatment can automatically be interrupted. With the aid of the display apparatus or another indication instrument it is possible instead to indicate when the value set has been reached, so that the attending physician can interrupt the supply of heat. Corresponding interruption or indication can also occur if the temperature measured or calculated in some part of the tissue exceeds a threshold value, or if other input data, such as, for example, the temperature in the rectum or in the bladder indicates a risk for the patient.

It is also possible continuously to alter certain settings during treatment, for example the desired temperature of treatment or the microwave input, without affecting or needing to change the value set for volume/weight. Instead the duration of treatment is affected. The duration of treatment can vary quite significantly with the method described above, depending on physiological differences and does not control the treatment in any decisive manner in comparison with methods of treatment employed previously.

Container 19 is completely closed and contains a certain volume of liquid 20 having suitable characteristics for heat transfer. Examples of such a liquid are silicon oil and water. Container 19 is made of elastic silicon or other material with corresponding elastic characteristics, for example, latex. Even catheters for treatment 12 and also balloon 29 can be made of silicon or similar material.

What is claimed is:

1. A device for supply of heat to body tissue, comprising a heating device arranged in a first end of a treatment catheter and a first temperature transducer arranged to be extended from the treatment catheter into body tissue, the heating device being connected to an energy supply unit via said treatment catheter and being controlled by a control unit, said treatment catheter being insertable in a body cavity and said first temperature transducer being operatively connected to the control unit, wherein a) said control unit is operatively connected to first memory means for storing data corresponding to a specific absorption rate (SAR) in body tissue caused by said heating device, b) an input device is operatively connected to said control unit for entering volume/weight data of body tissue that is intended to be treated, c) said control unit is operatively connected to calculation means for assessing volume and/or weight of said body tissue whose cells died as a function of temperature in the tissue at a certain distance from heating device.

2. The device according to claim 1, wherein said control unit is operatively connected to time-measuring means for continuously measuring a point of time when the tissue located at specific distances from heating device has reached a certain temperature.

3. The device according to claim 1, wherein said first memory means stores data related to the ability of specific body tissue to dissipate heat.

4. The device according to claim 1, wherein said first temperature transducer is designed to penetrate and to be inserted into the tissue to which heat is to be supplied.

5. The device according to claim 1, wherein a second temperature transducer is provided in the vicinity of heating device for measuring the temperature in the tissue close to said treatment catheter.

6. The device according to claim 5, wherein a third temperature transducer is designed to penetrate and be inserted into the tissue to which heat is to be supplied, to a distance from said treatment catheter that is between the first temperature transducer and the second temperature transducer.

7. The device according to claim 1, wherein said heating device comprises a microwave antenna for heating the surrounding tissue.

8. The device according to claim 7, wherein said heating device is arranged in a liquid container for heating liquid within said container and surrounding tissue.

9. The device according to claim 2, wherein said control unit is operatively connected to a display unit for presentation of the temperature in different parts of the tissue under treatment, and said calculation means is designed to determine the presented temperature on the basis of signals from said first temperature transducer and through calculation on the basis of how the tissue temperature is changed over time in the tissue in which the first temperature transducer is inserted.

10. A method for monitoring the progress of heat treatment of body tissue in terms of damage to the tissue, comprising the steps of:

a) determining a specific absorption rate (SAR) in body tissue caused by a heating device, b) heating said tissue by said heating device, c) measuring temperature in at least one location in said tissue, d) calculating temperature distribution in the tissue dynamically, and e) dynamically assessing on the basis of step d, elapsed time and known heat sensitivity of body tissue the amount of damaged tissue.

11. The method as claimed in claim 10, further comprising the step of:

considering the specific absorption rate and heat losses in the tissue due to heat conduction and blood flow when calculating the temperature distribution in the tissue.

12. A method for supplying heat to body tissue using a heating device and a first temperature transducer which is insertable in the body tissue, including the steps of:

a) enclosing the heating device in a catheter, b) connecting the heating device to an energy supply unit, c) measuring temperature in the body tissue with said first temperature transducer, d) determining temperature distribution in the body tissue on the basis of information on the measured temperature in the tissue and the distribution of energy absorption in the tissue, e) measuring elapsed time during which heat is supplied to the tissue, and f) calculating the amount of tissue destructed through energy absorption on the basis of the elapsed time and the temperature distribution.

13. The method for supply of heat to body tissue as claimed in claim 12, further comprising the steps of:

g) continuously presenting an image of the body tissue on a display unit, h) continuously calculating the temperature distribution in the tissue, and i) continuously displaying a representation of the temperature on the display unit.

14. The method for supply of heat according to claim 12, further comprising the steps of:

g) measuring a temperature outside tissue that is treated, and h) automatically interrupting the supply of heat if temperatures exceeding predetermined values in said tissue outside of the treated area are measured.

15. The method for supply of heat according to claim 12, further comprising the steps of:

g) storing in a first memory means data corresponding to the survival of cells as a function of cell temperature and time, said memory means being operatively connected to a control unit, h) entering data into an input device that is connected to said control unit, said data corresponding to desired volume and weight of the body tissue to which heat is to be supplied to an extent that the cells in the tissue die, and i) assessing in a calculation instrument a value corresponding to volume and weight of such body tissue whose cells died as a function of temperature in the tissue at a certain distance from heating device, said calculation instrument being operatively connected to said control unit.

* * * * *